United States Patent [19]

Dounchis

[11] 4,007,159
[45] Feb. 8, 1977

[54] ORGANIC SUBSTRATES STABILIZED BY NITROALKANE BASED HINDERED PHENOL COMPOUNDS

[75] Inventor: Harry Dounchis, Lawrenceville, N.J.

[73] Assignee: FMC Corporation, Philadelphia, Pa.

[22] Filed: Apr. 30, 1976

[21] Appl. No.: 681,837

Related U.S. Application Data

[63] Continuation-in-part of Ser. No. 475,318, May 31, 1974, abandoned.

[52] U.S. Cl. .............................. 260/45.9 E; 252/47; 260/810
[51] Int. Cl.² .......................................... C08K 5/32
[58] Field of Search .................... 260/45.9 E, 810; 252/47

[56] References Cited

UNITED STATES PATENTS

| | | | |
|---|---|---|---|
| 2,344,489 | 3/1944 | Boyer | 260/45.9 E |
| 3,236,667 | 2/1966 | Hodge et al. | 260/45.9 E |
| 3,364,172 | 1/1968 | Tocker | 260/45.9 E |
| 3,384,613 | 5/1968 | Parks | 260/45.9 E |
| 3,870,678 | 3/1975 | Harpell | 260/45.9 E |
| 3,903,049 | 9/1975 | Saltman et al. | 260/45.9 E |

*Primary Examiner*—V. P. Hoke
*Attorney, Agent, or Firm*—George F. Mueller; Frank Ianno; Pauline Newman

[57] ABSTRACT

Organic substrates stabilized against oxidative deterioration by the use of high molecular weight hindered phenols based on the condensation of a nitroalkane with either a dialkyldithiocarbonate or with formaldehyde and a di-t-butylphenol or a substituted derivative of a di-t-butylphenol.

10 Claims, No Drawings

ORGANIC SUBSTRATES STABILIZED BY NITROALKANE BASED HINDERED PHENOL COMPOUNDS

This application is a continuation-in-part of my copending application Ser. No. 475,318, filed May 31, 1974, now abandoned.

This invention relates to novel alkyl substituted phenol compounds. More particularly, this invention relates to novel di-tertiary-butyl substituted phenols, or hindered phenols, which are derived from reactions with a nitroalkane and which are highly effective antioxidants.

Phenolic antioxidants are commonly employed as stabilizers for a wide variety of organic substrates including natural and synthetic rubber, petroleum products such as lubricants, synthetic organic functional fluids and polymers and plastics such as polyolefins, polyvinyl chloride and the like. These phenolic antioxidants are generally the hindered phenols, that is, phenols containing alkyl substituents, as exemplified by 2,6-di-t-butyl-p-cresol, the alkyl-p-amino phenols, 4,4'-butylidiene bis(6-t-butyl-m-cresol) and the like.

Improved phenolic antioxidants are continually in demand, particularly improved antioxidants which are effective under conditions of extended use or high temperatures such as are encountered in petroleum oils and lubricants, hydraulic fluids, plastics and rubber, where the volatility of conventionally employed lower molecular weight materials is a disadvantage. It is an object of the present invention to provide relatively high molecular weight improved hindered phenolic antioxidants with a high degree of stabilizer activity.

Phenolic resins based on the reaction of phenol itself, formaldehyde and nitroparaffins are known and are described, for example, in U.S. Pat. Nos. 2,531,863 issued Nov. 28, 1950 to Scott et al, and 2,760,951 issued Aug. 28, 1956 to Park et al. However, the prior art fails to teach or suggest the novel compounds prepared in accordance with the present invention, nor is there any disclosure, so far as applicant is aware, of the advantage obtainable in employing the nitroalkane based hindered phenol antioxidants as described herein.

In accordance with the present invention, there are provided novel hindered phenolic compounds having the following general formulas:

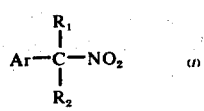
(I)

where Ar represents a 3,5-di-tertiarybutyl-4-hydroxybenzyl radical, $R_1$ and $R_2$ each may represent hydrogen, a lower $C_1$ to $C_4$ alkyl radical or an Ar radical as described above, and

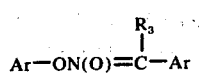
(II)

where Ar is as previously described and $R_3$ represents a lower $C_1$ to $C_4$ alkyl radical or a methoxy or ethoxy substituted $C_1$ to $C_4$ alkyl radical.

The novel compounds of the present invention are characterized as having a relatively low volatility and high molecular weight, when compared to conventional phenolic antioxidants.

The novel compounds of the present invention may be prepared by a number of suitable techniques. As described hereinafter, a nitroalkane may be reacted with formaldehyde and 2,6-di-t-butylphenol or a nitroalkane may be reacted with an intermediate, a 3,5-di-t-butyl-4-hydroxybenzyl N,N-dialkyl dithiocarbamate. A third technique is to condense a nitroalkane with a 4-alkoxymethyl-2,6-di-t-butylphenol. Nitromethane, nitroethane and both 1- and 2-nitropropane are particularly preferred reactants.

Suitable but less preferably techniques also include condensation reactions between a nitroalkane and other substituted derivatives of 4-methyl-2,6-di-t-butylphenol, the substituent replacing one or more of the hydrogens in the para-methyl group and being selected from the group consisting of halogen, alkylamino, hydroxy, thioalkyl and the like.

The preferred techniques for preparing the compounds of the present invention are considered to be novel processes and, as such, constitute further embodiments of the present invention. Thus, 2 or 3 moles of 2,6-di-t-butylphenol and 2 or 3 moles of formaldehyde may be condensed with 1 mole of a suitable nitroalkane. The reaction mixture is refluxed in an inert atmosphere for a period of about 1 to 25 hours and, at the completion of the reaction and cooling of the reaction mixture, the product crystallizes.

An alternate preferred procedure is to first prepare a 3,5-di-t-butyl-4-hydroxybenzyl N,N-dialkyldithiocarbamate. This intermediate is known as described, for example, in U.S. Pat. Nos. 3,260,756 and 3,260,758 both issued July 12, 1966 to O'Shea et al as well as in U.S. Pat. No. 3,117,947 issued Jan. 14, 1964 to Turner et al. The diethyldithiocarbamate is particularly useful in preparing the compounds of the present invention and is reacted with the desired nitroalkane in a molar ratio of about 1 to 3 moles per mol of nitroalkane.

The third preferred procedure is to react a nitroalkane, such as nitromethane, with about 1 to 3 moles of a 2,6-di-t-butyl-4-lower-alkoxymethylphenol, wherein the alkoxy may have up to about 4 carbon atoms and preferably is methoxy or ethoxy. The reaction is preferably carried out at the reflux temperature of the solvent and the product is obtained in a form of solid crystals.

The nitroalkanes as represented by Formula I are prepared by the reaction of nitromethane with either the described diethyldithiocarbamate or with a 2,6-di-t-butyl-4-lower-alkoxymethylphenol as described, or by the reaction of a secondary nitroalkane with either the diethydithiocarbamate or with formaldehyde and 2,6-di-t-butylphenol.

The nitronates as represented by Formula II are prepared by the reaction of a primary nitroalkane, except nitromethane, with either formaldehyde and 2,6-di-t-butylphenol or with the diethyldithiocarbamate, or by the reaction of nitromethane with formaldehyde, a lower aliphatic alcohol and 2,6-di-t-butylphenol.

The preferred reaction techniques described above for preparing the novel compounds of the present invention are all carried out in the presence of a polar, water miscible organic solvent. The reaction generally takes place at room temperature up to the reflux temperature of the solvent and this temperature range may be described as from about 25° to 100° C. Suitable solvents include the lower alkanols such as methanol, ethanol, propanol, isopropanol and the like as well as dimethyl sulfoxide, dioxane, tetrahydrofuran, and similar organic solvents. Methanol is particularly preferred. These reactions are also carried out in the presence of a basic catalyst such as an alkali metal or alkaline earth metal or ammonium oxide, carbonate or hydroxide, particularly sodium or potassium hydroxide. The amount of base used may vary from very minor catalytic amounts up to equimolar amounts or amounts substantially in excess of equimolar amounts. Other Bronsted bases are suitable. Exact amounts will depend on the particular reaction being employed. In some cases, the base may be functioning not only as a catalyst but also as a reactant. The use of molar excesses has not been found detrimental to the reaction technique and may be required in order to insure completion of the reaction. Generally speaking, about 1 to 150% by weight of the base catalyst, based on the weight of nitroalkane, may be employed. When the base is functioning only as a catalyst, the preferred quantity used is 2 to 10% by weight based on the weight of nitroalkane.

The novel compounds of the present invention are generally useful as antioxidants for stabilization of a wide variety of organic substrate materials, and are particularly suitable for use where service temperatures are relatively high or under other conditions wherein losses of more volatile antioxidants can occur. Thus, the novel compounds of the present invention may be used as stabilizers for natural rubber and synthetic rubbers such as polybutadiene rubber, styrene-butadiene rubber, polyisoprene rubber, neoprene rubber, butyl rubber, nitrile rubber, chloroprene rubber, ethylenepropylene-diene rubbers and the like. The compounds are also suitable for stabilization of polyolefins such as polyethylene, polypropylene, polybutene, polymethylbutene, polypentene, and copolymers of these olefin monomers such as ethylene-propylene copolymers and polymers of other polymerizable liquid ethylenically unsaturated monomers. Other plastics and resins which may be stabilized employing the compositions of the present invention include polystyrene, polyacrylates, polycarbonates, polyesters such as polyethylene terephthalate, polyvinyl chloride, polyvinyl acetate, polyamides, polyamines, polyacrylonitrile and similar polymers which are normally subject to oxidative deterioration.

Synthetic lubricants may also be stabilized and these include alkyl oxalates, malonates, and the like as well as polyol esters such as penterythritol, trimethylolpropane and sorbitol esters, alkyl esters of fatty acids such as lauric, oleic, palmitic, and stearic acids. Other synthetic lubricants and fluids include the polysiloxane oils, fluorocarbon lubricants, polyalkylene glycol lubricants such as copolymers of ethylene oxide and propylene oxide as well as triaryl phosphate ester functional fluids and lubricants.

Petroleum derived oils, fluids and lubricants may also be stabilized employing the novel antioxidants of the present invention and these organic substrates include industrial oils, turbine oils, transmission fluids, transformer oils, mineral oils and the like as well as fuels such as gasoline, jet fuel, diesel fuel and kerosene.

The compounds of the present invention are particularly suitable for the stabilization of polyolefin polymers, particularly polypropylene and for the stabilization of synthetic rubbers, and such stabilized compositions represent further preferred embodiments of the present invention.

The compounds of the present invention are generally employed in amounts ranging from 0.001 to 5 parts by weight per 100 parts of the organic materials being stabilized. Conventional techniques are employed to add the antioxidants to the organic substrate such as mixing or milling or use of a mutual solvent.

The invention is further illustrated by the following examples which should not be considered as limitative of its scope. The structure of all compounds was confirmed by IR and NMR spectroscopy. Temperatures reported are in degrees centigrade and percentages are by weight, unless otherwise stated.

EXAMPLE I

Preparation of Tris-(3,5-di-t-butyl-4-hydroxybenzyl)nitromethane.

To a rapidly stirred solution of 11.01 g of 3,5-di-t-butyl-4-hydroxybenzyl N,N-diethyldithiocarbamate in 100 ml of hot methanol was added a freshly prepared solution of 1.68 g of potassium hydroxide and 0.61 g of nitromethane. The resulting stirred mixture was refluxed under nitrogen for 24 hours. Upon cooling, 3.0 g of the product precipitated as white crystals, mp 199°–201° C. An additional 2.07 of pure product was obtained from the filtrate after recrystallization from acetonitrile and vacuum drying.

| Elemental Analysis: | Calcd. for $C_{46}H_{69}NO_5$: | %C, 77.17; |
|---|---|---|
| | | %H, 9.72; |
| | | %N, 1.96. |
| | Found: | %C, 77.05; |
| | | %H, 9.90; |
| | | %N, 2.12. |

EXAMPLE II

Preparation of 3,5-di-t-butyl-4-hydroxybenzyl 1-(3,5-di-t-butyl-4-hydroxybenzyl)-methoxypropane-2-nitronate.

2,6-di-t-butylphenol, 30.3 g, in 50 ml of methanol, was added at room temperature to a stirred solution of 24.3 g of 37% aqueous formaldehyde in 50 ml of methanol. A freshly prepared solution of 2.8 g of potassium hydroxide and 3.05 g of nitromethane was subsequently added. The resulting stirred solution was refluxed under nitrogen for 24 hours and kept at room temperature for 96 hours. The product, 5.2 g, mp 218°–220° C., was collected and washed with cold methanol and was recrystallized from acetonitrile and finally washed with hexane to obtain white crystals, mp 221°–2° C.

| Elemental Analysis: | Calcd. for $C_{33}H_{51}NO_5$: | %C, 72.76; |
|---|---|---|
| | | %H, 9.44; |
| | | %N, 2.56 |
| | Found: | %C, 73.16; |
| | | %H, 9.49; |
| | | %N, 2.59. |

EXAMPLE III

Preparation of 3,5-di-t-butyl-4-hydroxybenzyl 1-(3,5-di-t-butyl-4-hydroxybenzyl)-butane-2-nitronate.

a. To a stirred solution of 20.6 g of 2,6-di-t-butylphenol and 16.2 g of 37% aqueous formaldehyde (excess) in 75 ml of methanol was added at 25° C a freshly prepared solution of 4.5 g of nitropropane and 2.8 g of potassium hydroxide in 50 ml of methanol. The resulting stirred mixture was refluxed under nitrogen for 18 hours. A precipitate was observed to form after 35 minutes. The mixture was cooled in ice water and the crude product collected, mp 170°–8° C, and recrystallized from acetonitrile to yield 17.0 g of pure product, mp 176°–178° C.

b. 3,5-di-t-butyl-4-hydroxybenzyl N,N-diethyldithiocarbamate, 7.34 g in 100 ml of warm ethanol containing 0.89 g of nitropropane was treated with 1.17 of KOH in 100 ml of warm ethanol. The resulting stirred solution was refluxed under nitrogen for 16 hours. The reaction mixture was concentrated and extracted with hexane from which was obtained, after initial precipitation of a salt, 2.35 g of product. Two recrystallizations from acetonitrile afforded the product, mp 177°–180° C., identical to that obtained by procedure (a).

| Elemental Analysis: | Calcd. for $C_{33}H_{51}NO_4$: | %C, 75.38; %H, 9.78; %N, 2.66. |
|---|---|---|
| | Found: | %C, 75.34; %H, 9.74; %N, 3.26. |

EXAMPLE IV

Preparation of 3,5di-t-butyl-4-hydroxybenzyl 1-(3,5-di-t-butyl-4-hydroxybenzyl)-propane-2-nitronate.

To a stirred solution of 2,6-di-t-butylphenol, 20.6 g, and 37% aqueous formaldehyde, 16.2 g (excess), in 100 ml of methanol was added a freshly prepared solution of 5.6 g of potassium hydroxide and 3.75 g of nitroethane in 75 ml of methanol. The reaction mixture was heated to reflux under nitrogen for 17 hours. A precipitate began to form after one hour. The product was collected and washed with cold methanol giving 17.3 g of pure product, mp 208°–210° C.

| Elemental Analysis: | Calcd. for $C_{32}H_{49}O_4N$: | %C, 75.10; %H, 9.65; %N, 2.74. |
|---|---|---|
| | Found: | %C, 75.32; %H, 9.82; %N, 2.68. |

EXAMPLE V

Preparation of 2,6-di-t-butyl-4-(2-methyl-2-nitropropyl)phenol.

2,6-di-t-butylphenol, 20.6 g, in 100 ml of stirred methanol containing 16.2 g of 37% aqueous formaldehyde (excess) was treated with a freshly prepared solution of 5.6 g of potassium hydroxide and 8.9 g of 2-nitropropane and heated under nitrogen for 2½ hours. Upon cooling, 19.8 g of product, mp 101°–4° C., was obtained in two crops. Recrystallization from methanol afforded product melting 103.5°–105.5° C.

| Elemental Analysis: | Calcd. for $C_{18}H_{29}NO_3$: | %C, 70.32; %H, 9.51; %N, 4.56. |
|---|---|---|
| | Found: | %C, 70.60; %H, 9.41; %N, 4.49. |

EXAMPLE VI

Preparation of 1,3-bis(3,5-di-t-butyl-4-hydroxyphenyl)-2-nitropropane.

To a solution of 14.5 g (0.22 mole) of 85% potassium hydroxide in 300 ml of methanol was added in a stream of nitrogen to exclude air 13.4 g (0.22 mole) of nitromethane and 50.0 g (0.2 mole) of 2.6-di-t-butyl-4-methoxymethylphenol. The magenta solution was stirred for one hour at reflux, with exclusion of air. After cooling somewhat, the solution was neutralized with 13 ml of acetic acid and chilled. A thick paste formed which was filtered, washed and dried. The resulting tan powder (48.1 g, mp 152°–154° C) was recrystallized from 500 ml of heptane, after filtering insoluble matter (10.4 g). The yield of tan crystals was 32.3 g, mp 161°–165° C.

| Elemental Analysis: | Calcd. for $C_{31}H_{47}NO_4$: | %C, 74.81; %H, 9.42; %N, 2.82. |
|---|---|---|
| | Found: | %C, 74.80; %H, 9.92; %N, 2.73. |

EXAMPLE VII

The use of these compounds as antioxidants is demonstrated by the ASTM D943 oxidation test for turbine oils. The results are set out in Table 1.

Table 1

| Compound | % Conc. | Hours to Failure |
|---|---|---|
| Blank | | <125 |
| Tris-(3,5-di-t-butyl-4-hydroxybenzyl) nitromethane | 0.5 | 2,051 |
| 3,5-di-t-butyl-4-hydroxybenzyl 1-(3,5-di-t-butyl-4-hydroxybenzyl)propane-2-nitronate | 0.5 | 1,419 |
| 3,5-di-t-butyl-4-hydroxybenzyl 1-(3,5-t-butyl-4-hydroxybenzyl)butane-2-nitronate | 0.1 | >400 |
| 2,6-di-t-butyl-4-(2-methyl-2-nitropropyl)phenol | 0.1 | >400 |
| 3,5-di-t-butyl-4-hydroxybenzyl 1-(3,5-di-t-butyl-4-hydroxybenzyl)-3-methoxypropane-2-nitronate | 0.1 | >400 |

EXAMPLE VIII

The usefulness of the compounds of this invention as antioxidants in a triaryl phosphate fluid is demonstrated in this example. A commercial triaryl phosphate, Kronitex 100 (FMC Corp.), a mixed isopropylphenyl/phenyl phosphate produced by phosphorylation of phenol alkylated with about 30% by weight propylene containing 0.1% of two representative compounds of this invention was evaluated via the ASTM D2272 Rotary Bomb Oxidation Stability Test. The induction period is a measure of the rate of oxygen consumption in a sealed, pressurized bomb. The results are as follows:

| Compound | Induction Period (minutes) |
|---|---|
| Blank | 94 |
| Tris(3,5-di-t-butyl-4-hydroxy- | |

-continued

| Compound | Induction Period (minutes) |
|---|---|
| benzyl)nitromethane | 240 |
| 3,5-di-t-butyl-4-hydroxy-benzyl 1-(3,5-di-t-butyl-4-hydroxybenzyl)propane-2-nitronate | 235 |

EXAMPLE IX

The compounds of Example VIII were shown via the ASTM D2272 Rotary Bomb Oxidation Stability Test to impart enhanced oxidative stability when added to a commercial uninhibited 5 centistoke synthetic ester lubricant (pentaerythritol ester of mixed $C_5$–$C_{10}$ carboxylic acids).

EXAMPLE X

In order to demonstrate the effectiveness of the antioxidants of this invention in improving the oxidation stability of polypropylene "Oven Aging Test" were conducted in an air circulating oven maintained at 150° C. Samples of unstabilized polypropylene homopolymer molding powder (Hercules Profax 6401) containing the compounds of this invention alone and in combination with DLDTP (dilauryl 3,3-thiodipropionate), a synergist for hindered phenol antioxidants, were evaluated. BHT (2,6-di-t-butyl-4-methylphenol), a commercial antioxidant, was included. Five replicates of each polypropylene-stabilizer composition were prepared and the test criteria is the average time to deterioration of the five samples as evidenced by crazing on the surface.

Test specimens were prepared by mixing the polypropylene and stabilizer system in a blender followed by banding at 350° F and fluxing at 310° F on a two roll mill for less than 10 minutes. The resulting samples were pressed at 310° F under 1700 to 2800 psi pressure into 6 × 6 inch sheets, 0.0075 inch thick. The sheets were cut and trimmed into test specimens 1 × ½ inches. The following Table 2 summarizes the results:

Table 2

| Sample | Antioxidant | Oven Aging Tests Synergist | Hours to Failure |
|---|---|---|---|
| (a) | None | None | 75 |
| (b) | BHT | None | 15 |
| (c) | BHT | DLTDP | 39 |
| (d) | None | DLTDP | 137 |
| (e) | Ex. 1 | None | 143 |
| (f) | Ex. 1 | DLTDP | 359 |
| (g) | Ex. 2 | None | 66 |
| (h) | Ex. 2 | DLTDP | 303 |
| (i) | Ex. 4 | None | 61 |
| (j) | Ex. 4 | DLTDP | 215 |
| (k) | Ex. 3 | None | 61 |
| (l) | Ex. 3 | DLTDP | 153 |
| (m) | Ex. 5 | None | 19 |
| (n) | Ex. 5 | DLTDP | 42 |

In each sample, the antioxidant concentration was 0.1 parts per hundred parts (phr) of polypropylene. When present, the synergist was used at a concentration of 0.2 phr. Samples (e) – (n) employed compounds of the invention and refer to compounds illustrated in Examples 1–5.

The formulas and compound names for particularly preferred embodiments of the present invention are set forth in the following Tables I and II.

Table I

| Formula | Name |
|---|---|
| 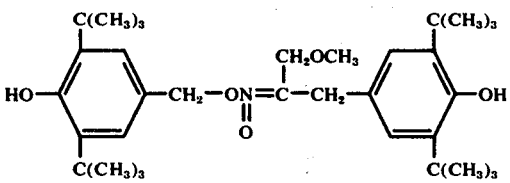 | 3,5-di-t-butyl-4-hydroxybenzyl 1-(3-5-di-t-butyl-4-hydroxybenzyl)-3-methoxypropane-2-nitronate |
| 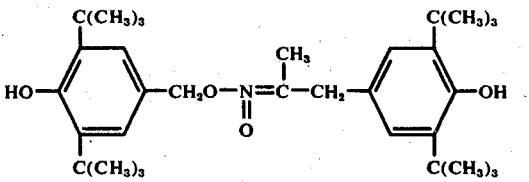 | 3,5-di-t-butyl-4-hydroxybenzyl 1-(3,5-di-t-butyl-4-hydroxybenzyl)-propane-2-nitronate |
| 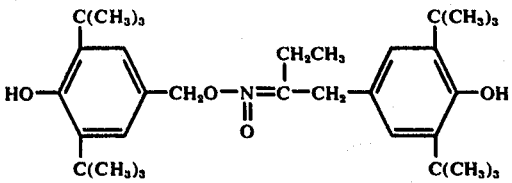 | 3,5-di-t-butyl-4-hydroxybenzyl 1-(3,5-di-t-butyl-4-hydroxybenzyl)-butane-2-nitronate |

Table II

| Formula | Name | Formula | Name |
|---|---|---|---|
|  | 2,6-di-t-butyl-4-(2-methyl-2-nitropropyl)phenol |  | Tris-(3,5-di-t-butyl-4-hydroxybenzyl)nitromethane |
|  | 1,3-bis(3,5-di-t-butyl-4-hydroxyphenyl)-2-nitropropane | | |

What is claimed is:

1. Stabilized compositions comprising an organic material normally susceptible to oxidative deterioration containing per 100 parts of said organic material from about 0.001 to 5 parts by weight of a stabilizing antioxidant compound selected from the group having the formulas:

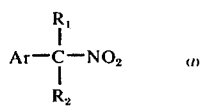

wherein Ar represents a 3,5-di-tertiary-butyl-4-hydroxybenzyl radical, $R_1$ and $R_2$ each may represent hydrogen, a lower $C_1$–$C_4$ alkyl radical or an Ar radical, and

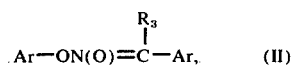

wherein Ar is as previously described and $R_3$ represents a lower $C_1$–$C_4$ alkyl or a methoxy or ethoxy substituted lower $C_1$–$C_4$ alkyl radical.

2. The composition of claim 1 wherein the organic material is a synthetic rubber.
3. The composition of claim 1 wherein the organic material is a polyolefin homopolymer or copolymer.
4. The composition of claim 1 wherein the organic material is polypropylene.
5. The composition of claim 1 wherein the stabilizing antioxidant is 2,6-di-t-butyl-4(2-methyl-2-nitropropyl)phenol.
6. The composition of claim 1 wherein the stabilizing antioxidant is 1,3-bis(3,5-di-t-butyl-4-hydroxyphenyl)-2-nitropropane.
7. The composition of claim 1 wherein the stabilizing antioxidant is tris-(3,5-di-t-butyl-4-hydroxybenzyl) nitromethane.
8. The composition of claim 1 wherein the stabilizing antioxidant is 3,5-di-t-butyl-4-hydroxybenzyl 1-(3,5-di-t-butyl-4-hydroxybenzyl)-methoxypropane-2-nitronate.
9. The composition of claim 1 wherein the stabilizing antioxidant is 3,5-di-t-butyl-4-hydroxybenzyl 1-(3,5-di-t-butyl-4-hydroxybenzyl)-propane-2-nitronate.
10. The composition of claim 1 wherein the stabilizing antioxidant is 3,5-di-t-butyl-4-hydroxybenzyl 1-(3,5-di-t-butyl-4-hydroxybenzyl)-butane-2-nitronate.

* * * * *